United States Patent [19]

Jackson

[11] 4,064,126
[45] Dec. 20, 1977

[54] PROCESS FOR THE PRODUCTION OF OROTIC ACID

[75] Inventor: Barry Jackson, Visp, Switzerland

[73] Assignee: Lonza, Ltd., Gampel, Switzerland

[21] Appl. No.: 713,577

[22] Filed: Aug. 11, 1976

[30] Foreign Application Priority Data

Aug. 11, 1975 Switzerland ............ 010418/75

[51] Int. Cl.² .......................................... C07D 239/54
[52] U.S. Cl. ................................................ 260/260
[58] Field of Search ........................................ 260/260

[56] References Cited

U.S. PATENT DOCUMENTS 3,838,128  9/1974  Lutz et al. ...................... 260/260

FOREIGN PATENT DOCUMENTS 2,025,247  12/1970  Germany.

Primary Examiner—Paul M. Coughlan, Jr.
Attorney, Agent, or Firm—Virgil H. Marsh

[57] ABSTRACT

A process for the production of orotic acid which comprises (a) converting trichloroacetyl chloride to $\gamma, \gamma, \gamma$-trichloroacetoacetyl chloride with ketene, (b) adding reaction mixture (a) to urea dissolved in a polar organic solvent, e.g., acetic acid, 6-trichloromethyluracil being produced, (c) separating the 6-trichloromethyluracil from reaction mixture (b), and (d) hydrolyzing the 6-trichloromethyluracil to orotic acid.

16 Claims, No Drawings

PROCESS FOR THE PRODUCTION OF OROTIC ACID

BACKGROUND OF THIS INVENTION

1. Field of This Invention

This invention relates to a process for the production of orotic acid.

2. Prior Art

German OS No. 2,025,247 teaches that orotic acid can be prepared by converting, in a first stage, diketene and chlorine to γ-chloroacetoacetic acid chloride, in a second stage, reacting the γ-chloroacetoacetic acid chloride with urea to form 6-chloromethyluracil, separating the 6-chloromethyluracil and oxidizing the 6-chloromethyluracil with hydrogen peroxide to orotic acid.

BROAD DESCRIPTION OF THIS INVENTION

An object of this invention is to provide a new process for the production of orotic acid in a high yield.

Other objects and advantages of this invention are set out herein or are obvious herefrom to one ordinarily skilled in the art.

The objects and advantages of this invention are achieved by the process of this invention.

It has been found that orotic acid can be produced, with good yields, starting from trichloroacetyl chloride and ketene.

This invention involves a process for the production of orotic acid. The process includes (a) converting trichloroacetyl chloride to γ,γ,γ-trichloroacetoacetyl chloride using ketene, (b) adding reaction mixture (a) to urea dissolved in a polar organic solvent, 6-trichloromethyluracil being produced, (c) separating the 6-trichloromethyluracil from reaction mixture (b), and (d) hydrolyzing the 6-trichloromethyluracil to orotic acid.

Step (a) of the reaction, that is the production of γ,γ,γ-trichloroacetoacetyl chloride from trichloroacetyl chloride and ketene, can be effected temperatures the presence of an organic solvent and an acidic catalyst. Such so-called insertion reactions are known, for example, from German Pat. No. 1,041,030. The best results however are obtained without the use of a solvent or a catalyst by directly leading the ketene into the trichloroacetyl chloride at temperatures between $-20°$ and $-40°$ C.

In step (b) of the process, urea is suspended in a polar organic solvent, preferably a lower carboxylic acid and most preferably acetic acid, at temperature between 20° and 40° C. The reaction mixture of step (a), containing the γ,γ,γ-trichloroacetoacetyl chloride, is supplied with an excess of moisture to the urea suspension. During this addition there is cooling so that the temperature will not exceed 40° C. Subsequently the reaction mixture is heated to 100° to 120° C., whereupon the 6-trichloromethyluracil is precipitated upon cooling as a solid precipitate and can be separated out by any convenient method.

Advantageously the urea is used in two to four times the stoichiometric quantity, based on the trichloroacetyl chloride.

The hydrolysis of the 6-trichloromethyluracil is advantageously conducted under neutral conditions or at weakly basic conditions. In a preferred embodiment, 6-trichloromethyluracil is reacted at a pH of 6 to 7 in water at temperatures between 15° and 100° C. The pH is sustained by the addition of sodium hydroxide. The precipitated salt of orotic acid can be converted to free orotic acid by treatment with a mineral acid, for example, sulfuric acid, hydrochloric acid, etc.

This invention also includes 6-trichloromethyluracil, which has the formula:

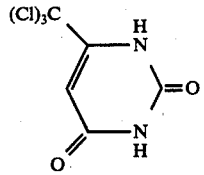

DETAILED DESCRIPTION OF THIS INVENTION

Orotic acid is 6-uracilcarboxylic acid and has the structural formula:

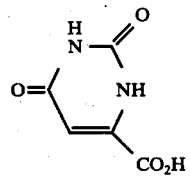

Examples of the organic solvent that can be used in step (a) are acetone, acetyl acetone, adiponitrile, 2-amino-2-methyl-1-propanol, benzene, benzin, benzonitrile, benzothiazole, benzyl alcohol, benzyl mercaptan, butyl acetate, butyl alcohol, capryl alcohol, carbon te-rachloride, diacetone alcohol, diethanolamine, diethyl Cellosolve, diethyl ether, dimethylaniline, di-N-propylaniline, ethanol, ethyl benzoate, ethyl isothiocyanate, ethyl thiocyanate, ethylene glycol, 2-ethylhexanol, formamide, furfuryl alcohol, glycerol, hydroxyethylethylenediamine, isoamyl alcohol, isoamyl sulfide, isobutyl mercaptan, methyl disulfide, nitromethane, dibutoxytetraethylene glycol, pyridine, tri-n-butylamine and trimethylene glycol.

The lower carboxylic acid solvent (polar) used in step (b) preferably has one to five carbon atoms. Examples of the lower (aliphatic) carboxylic acid are formic acid, acetic acid, propionic acid, butyric acid, valeric acid, caproic acid and enanthic acid. Anhydrous acetic acid is preferred.

Examples of useful mineral (inorganic) acids are sulfuric acid (preferred), phosphoric acid, hydrochloric acid, sulfurous acid, phosphorous acid, nitric acid, nitrous acid, boric acid and hydrofluoric acid.

To recap, this invention involves: converting trichloroacetyl chloride with ketone to γ,γ,γ-trichloroacetoacetyl chloride, adding the reaction mixture to urea dissolved in a polar organic solvent, e.g., acetic acid; evaporating out the resulting 6-trichloromethyluracil; and hydrolyzing the 6-trichloromethyluracil to form orotic acid.

As used herein, all parts, percentages and ratios are on a weight basis, unless otherwise stated herein or otherwise obvious herefrom to one ordinarily skilled in the art.

EXAMPLE i. Production of γγ,γ-trichloroacetoacetylchloride (insertion reaction):

91.7 gm (0.5 mole) of trichloroacetylchloride was cooled to −35° C. in a glass vessel by means of a cooling brine. In the course of 3 hours, 27.0 gm. (0.06 mole) of pure ketene was introduced through a tube. After completion of the reaction, the vessel was immediately put under dry nitrogen to prevent penetration of moisture.

ii. Production of 6-trichloromethyluracil:

The reaction mixture of the insertion insertion (i) that contained γ,γγ-trichloroacetoacetylchloride was transfered under nitrogen to a dropping funnel and in the course of 15 minutes was added with vigorous agitation to a suspension of 69 gm. (1.15 mole) of urea in 90 gm. of anhydrous acetic acid. Water cooling was used so that the reaction temperature would not exceed 40° C. After completion of the addition, the reaction mixture was heated as rapidly as possible to 115° C, and held at this temperature for 30 minutes. Subsequently there was cooling and one more 99 gm. of glacial acetic acid and 180 gm. of water were added. The precipitated 6-trichloromethyluracil was filtered off and dried at 60° C. in a vacuum drying cabinet. The yield was 91 gm. or 80 percent, based on the trichloroacetylchloride used in the insertion reaction.

Since this involved a compound not previously described in the literature, that is 6-trichloromethyluracil, the structure was confirmed with IR and NMR spectroscopy.

Elemental analysis:

| | C | H | Cl | N |
|---|---|---|---|---|
| Calculated for $C_5H_3Cl_3N_2O_2$ | 26.2% | 1.3% | 46.4% | 12.2% |
| found | 26.3% | 1.4% | 46.2% | 11.8% | iii. Hydrolysis of 6-trichloromethyluracil to orotic acid:

In a glass vessel equipped with an agitator, thermometer and pH electrode, 500 cm³ of water was placed and heated to 80° C. 50 gm. of 6-trichloromethyluracil was then added. By means of the pH electrode, the addition of sodium hydroxide was automatically controlled so that the pH value throughout the whole hydrolysis was 6.5. In toto, 165 cm³ of 5N NaOH was consumed. Finally, the hydrolysis solution was cooled and the precipitated sodium orotate filtered off.

The crude sodium orotate was again suspended at 80° C. in water and brought into solution (pH 10.5) by addition of 30 cm³ of 5N NaOH. After treatment with active charcoal, the solution was acidified with 30 gm. of 50 percent sulfuric acid. The solution was then cooled. The orotic acid was filtered off and carefully washed with water. After drying, 20.5 gm. of orotic acid, having a purity of 99.3 percent (titration) was obtained. This corresponds to a 60 percent yield, based on the 6-trichloromethyluracil.

What is claimed is:

1. The process for the production of orotic acid, which comprises (a) converting trichloroacetyl chloride to γ,γ,γ-trichloroacetoacetyl chloride with ketone, (b) adding reaction mixture (a) to urea dissolved in a polar organic solvent, 6-trichloromethyluracil being produced, (c) separating the 6-trichloromethyluracil from reaction mixture (b), (d) hydrolyzing the 6-trichloromethyluracil to the salt of orotic acid at neutral or weakly basic conditions, and (e) treating the salt of orotic acid with a mineral acid, whereby free orotic acid is produced.

2. The process as claimed in claim 1 wherein an organic solvent and an acidic catalyst are present in step (a).

3. The process as claimed in claim 1 wherein step (a) is conducted, in the absence of any organic solvent and any acidic catalyst, at a temperature between −20° and −40° C.

4. The process as claimed in claim 1 wherein the polar organic solvent in step (b) is a lower carboxylic acid.

5. The process as claimed in claim 1 wherein the polar organic solvent in step (b) is acetic acid.

6. The process as claimed in claim 1 wherein step (b) is conducted at a temperature not exceeding 40° C. while the γ,γ,γ-trichloroacetoacetyl chloride is added to the urea solution and then the resultant reaction mixture is heated to 100° to 120° C.

7. The process as claimed in claim 6 wherein, after heating to 100° to 120° C., the reaction mixture is cooled, with the resultant 6-trichloromethyluracil precipitating as a solid.

8. The process as claimed in claim 1, wherein, in step (b), the urea is used in a quantity which is two to four times the stoichiometric amount, based on the amount of trichloroacetyl chloride used.

9. The process as claimed in claim 1 wherein the urea solution used in step (b) is at a temperature between 20° and 40° C.

10. The process as claimed in claim 1 wherein the hydrolysis of step (d) is conducted at a neutral pH or a weakly basic pH.

11. The process as claimed in claim 1 wherein the hydrolysis of step (d) is conducted in an aqueous solution at a pH of 6 to 7 at a temperature between 15° and 100° C.

12. The process as claimed in claim 1 wherein the salt of orotic acid obtained from step (d) is converted to free orotic acid by treatment with a mineral acid.

13. The process as claimed in claim 1 wherein the mineral acid is sulfuric acid.

14. 6-trichloromethyluracil.

15. The process as claimed in claim 1 wherein step (a) is conducted, in the absence of any organic solvent and any acidic catalyst, at a temperature between −20° and −40° C, wherein step (b) is conducted at a temperature between 20° and 40° C. while the γ,γ,γ-trichloroacetoacetyl chloride is added to ,γ,γthen the resultant reaction mixture is heated to 100° to 120° C., the urea is used in a quantity which is two to four times the stoichiometric amount, based on the amount of trichloroacetyl chloride used, wherein, after heating to 100° to 120° C. in step (b), step (c) is conducted by cooling the reaction mixture, the resultant 6-trichloromethyluracil precipitating as a solid, and separating out the precipitated 6-trichloromethyluracil, wherein the hydrolysis of step (d) is conducted in an aqueous solution at a pH of 6 to 7 at a temperature between 15° and 100° C., and wherein the salt of orotic acid obtained from step (d) is converted to free orotic acid by treatment with a mineral acid.

16. The process as claimed in claim 1 wherein an organic solvent and an acidic catalyst are present in step (a), is conducted, in the absence of any organic solvent and any acidic catalyst, at a temperature between −20° and −40° C., wherein step (b) is conducted at a temperature between 20° and 40° C. while the γ, γ, γ-trichloroacetoacetyl chloride is added to the urea solution and then the resultant reaction mixture is heated to 100° to 120° C., the urea is used in a quantity which is two to four times the stoichiometric amount, based on the amount of trichloroacetyl chloride used, wherein after heating to 100° to 120° C. in step (b), step (c) is conducted by cooling the resultant 6-trichloromethyluracil precipitating as a solid, and separating out the precipitated 6-trichloromethyluracil, wherein the hydrolysis of step (d) is conducted in an aqueous solution at a pH of 6 to 7 at a temperature between 15° and 100° C., and wherein the salt of orotic acid obtained from step (d) is converted to free orotic acid by treatment with a mineral acid.

* * * * *